US006989278B1

(12) United States Patent
Clancy et al.

(10) Patent No.: US 6,989,278 B1
(45) Date of Patent: Jan. 24, 2006

(54) METHOD OF IDENTIFYING THERAPEUTIC COMPOUNDS FOR A TREATMENT OF HEPATIC DISORDERS

(75) Inventors: Robert Clancy, Newcastle (AU); Robert Batey, Charlestown (AU); Gerald Pang, Elizabeth Bay (AU)

(73) Assignee: The University of Newcastle Research Associates Limited, Callaghan (AU)

( * ) Notice: Subject to any disclaimer, the term of this patent is extended or adjusted under 35 U.S.C. 154(b) by 0 days.

(21) Appl. No.: 09/959,970

(22) PCT Filed: May 15, 2000

(86) PCT No.: PCT/AU00/00440

§ 371 (c)(1),
(2), (4) Date: Mar. 15, 2002

(87) PCT Pub. No.: WO00/69451

PCT Pub. Date: Nov. 23, 2000

(30) Foreign Application Priority Data

May 14, 1999 (AU) ..................................... PQ0376

(51) Int. Cl.
*G01N 33/53* (2006.01)
(52) U.S. Cl. ...................................................... 436/811
(58) Field of Classification Search ................. 424/9.2
See application file for complete search history.

(56) References Cited

FOREIGN PATENT DOCUMENTS

WO    WO 96 01115    1/1996

OTHER PUBLICATIONS

Grant & Hackh's chemical Dictionary, Fifth Edition. eds. Grant et al., McGraw-Hill Book Company, p. 143.*
Barrio et al., "Comparative Effect of Nifedipine and S-Adenosylmethionine, Singly and in Combination on Experimental Rat Live Cirrhosis", Life Sciences 52 (20) : PL217-220 (1993).*
Manna et al., "Effects of Hepatic Stimulator Substnace, Herbal Medicine, Selenium/VitaminE, and Ciprofloxacin on Cirrhosis in the Rat", Gastroenterology 110 : 1150-55 (1996).*
Cao et al, *Alcoholism: Clinical and Experimental Research*, 22:723-729 (1998).
Batey et al, *Alcoholism: Clinical and Experimental Research*, 22:150-156 (1998).
Cao et al, *Alcoholism: Clinical and Experimental Research*, 23(10):1660-1667 (1999).
Roselle et al, *Alcoholism: Clinical and Experimental Research*, 8(1):62-67 (1984).
Cao et al, *Immunology and Cell Biology*, 76:542-549 (1998).
Batey et al, *Journal of Gastroenterology and Hepatology*, 13:244-247 (1998).
Spinozzi et al, *Immunology*, 73:140-146 (1991).
Roselle et al, *Alcohol Clin. Exp. Res.*, 49(3):551-554 (1995).
McKeever et al, *Clin. Exp. Immunology*, 60:39-48 (1995).
Winnock et al, *J. of Gastroenterology and Hepatology*, 10:S43-S46 (1995).
Wang et al, *Alcohol Clin. Exp. Res.*, 18(1):64-70 (1994).
Chedid et al, *Gastroenterology*, 105:254-266 (1993).
Khoruts et al, *Hepatology*, 13(2):267-276 (1991).
Keegan et al, *J. of Hepatology*, 23:591-600 (1995).
Mizuhara et al, *J. Exp. Med.*, 179:1529-1537 (1994).
Noble et al, *J. of Immunology*, pp. 2928-2937 (1995).
van Leeuwen et al, *Scand. J. Gastroenterol.*, 24(1):65-73 (1989).
Leon et al, *Clin. Exp. Immunol.*, 99(2):233-239 (1995).
Jones et al, *Hepatology*, 21(4):995-1002 (1995).
Hoso et al, *Pathol. Int.*, 46(4):301-305 (1996).
Himmelmann et al, *J. Lab. Clin. Med.*, 133(3):229-236 (1999).

* cited by examiner

Primary Examiner—Sandra E. Saucier
(74) Attorney, Agent, or Firm—Sughrue Mion, PLLC (57) ABSTRACT

The present invention relates to methods of identifying potentially therapeutic compounds for the treatment of hepatic disorders, preferably alcohol-induced hepatitis. Further, use of mammals in such methods, therapeutic compounds identified using said methods and the use of a Chinese Herb, CH-100, in the treatment of hepatic disorders, particularly alcohol-induced hepatic disorders, are described.

13 Claims, 4 Drawing Sheets

METHOD OF IDENTIFYING THERAPEUTIC COMPOUNDS FOR A TREATMENT OF HEPATIC DISORDERS

This application is a National Stage filing under 35 U.S.C. § 371 of PCT/AU00/00440, filed May 15, 2000. The disclosure of which is incorporated herein by reference.

TECHNICAL FIELD

The present invention relates to a method of identifying therapeutic compounds and in particular to a method of identifying therapeutic compounds for use in treating hepatic disorders.

BACKGROUND

Hepatic disease is a major cause of morbidity in western countries. Hepatitis C, for example, is transmitted by blood contamination and many current cases represent infection from blood transfusion prior to universal blood testing. Most new cases are drug (of addiction) related. About 80% of those affected develop chronic hepatitis (20% with cirrhosis) while about 10% will eventually develop hepatoma. Until recently, the only effective therapy has been interferon, which is expensive, is given parentally, has many side effects, and is of limited value.

Alcohol consumption can lead to hepatic disorders. It affects normal immune function, especially cell-mediated immunity[1-3]. T cells play an important role in the progression of alcohol-related disease[4-6]. Studies of alcoholic liver disease in humans and animals have shown that T cell proliferation is significantly altered in response to mitogens such as concanavalin A (Con A) or phytohemagglutinin (PHA) in vitro[7-9]. In rats or mice fed alcohol, the blood T cell proliferative response to Con A stimulation was depressed whereas the response to PHA was elevated, with $CD4^+$ T helper cells being the responding cell type[2,3,8,10]. This suggests that the level of T-cell activation[10], the responding cell phenotype[3], and the pattern of cytokine secretion[1F] following exposure to ethanol probably all play a role in alcohol related liver disease. Ethanol-fed rats injected with Con A developed more severe hepatic necrosis with infiltration of $CD4^+$ and $CD8^+$ T cells in the portal vein and central vein areas compared with sucrose or isocaloric sucrose fed rats. In these rats increased numbers of activated liver-associated $CD4^+$ T cells secreting high levels of TNF-α and IL-6 in culture were observed[4-6]. These alcohol-fed rats have been used as a basic research tool to study the role of T lymphocytes in the onset of liver damage.

While it is hypothesised that the level of T-cell activation, the responding cell phenotype, and the pattern of cytokine secretion following exposure to ethanol may all play a role in alcohol-associated liver disease, it is noted that such diseases are complex in nature. As such many other as yet unidentified factors are likely to contribute to the presentation of the disease. Thus, further research is necessary to elucidate the precise cellular and biochemical mechanisms and interactions involved in the initiation and progression of the disease. Further, it is noted that the precise cellular and biochemical mechanisms and interactions involved in alcohol-induced hepatitis are likely to be different to the precise mechanisms involved in pathogen-mediated hepatitis, such as hepatitis C, and auto-immune hepatic disorders.

Treatment for many hepatic disorders is clearly unsatisfactory and there is an urgent need for improved therapeutics. Consequently there is also a need for suitable methods and in particular animal models to predict the therapeutic value of potentially useful compounds.

It is an object of the present invention to provide an animal model, methods and therapeutic compounds which may overcome or substantially ameliorate at least some of the deficiencies of the prior art, or will provide a useful alternative.

SUMMARY OF THE INVENTION

It has been found that mammals administered alcohol and an agent such as concanavalin A (Con A) are useful as a model for identification of therapeutic substances destined to treat hepatic disorders.

It has also been found that the Chinese herb CH-100 is particularly useful in the treatment of alcohol-induced hepatitis.

According to a first aspect, the invention provides a method of identifying a compound useful in the prophylactic or therapeutic treatment of a hepatic disorder in a mammal comprising:
  (a) administration to the mammal of an agent or agents known to induce a hepatic disorder;
  (b) administration to a mammal of a potentially therapeutic compound;
  (c) comparison of the effects of the compound on the development of the hepatic disorder with a predetermined standard.

According to a second aspect, the invention provides a method of identifying a compound useful in the prophylactic or therapeutic treatment of a hepatic disorder in a mammal comprising:
  (a) administration to the mammal of alcohol;
  (b) administration to the mammal of a potentially therapeutic compound;
  (c) administration to the mammal of an agent known to induce a hepatic disorder; and
  (d) comparison of the effects of the compound on the development of the hepatic disorder with a predetermined standard.

According to a third aspect, the invention provides a method of identifying a compound useful in the prophylactic or therapeutic treatment of T cell-mediated liver damage in a mammal comprising:
  (a) administration to the mammal of an agent or agents known to induce T cell-mediated liver damage;
  (b) administration to the mammal of a potentially therapeutic compound;
  (c) comparison of the effects of the compound on the development of the liver damage with a predetermined standard.

According to a fourth aspect, the invention provides a method of identifying a compound useful in the prophylactic or therapeutic treatment of T cell-mediated liver damage in a mammal comprising:
  (a) administration to the mammal of alcohol;
  (b) administration to the mammal of a potentially therapeutic compound;
  (c) administration to the mammal of a T cell activating agent; and
  (d) comparison of the effects of the compound on the development of the hepatic disorder with a predetermined standard.

According to a fifth aspect, the invention provides a method of identifying a compound useful in the prophylactic or therapeutic treatment of T cell-mediated liver damage in a mammal comprising:
(a) administration to a donor mammal of alcohol;
(b) administration to a donor mammal of a T cell-activating agent;
(c) administration of a potentially therapeutic compound to a recipient mammal;
(d) isolation of intrahepatic T cells from the donor mammal and delivery to the recipient; and
(e) comparison of the effects of the compound on the development of T cell-mediated liver damage in the recipient mammal with a predetermined standard.

According to a sixth aspect, the invention provides a method of identifying a compound useful in the prophylactic or therapeutic treatment of T cell-mediated liver damage in a mammal comprising:
(a) administration to a donor mammal of alcohol;
(b) administration to a donor mammal of a T cell-activating agent;
(c) isolation of intrahepatic T cells from the donor mammal and delivery to a recipient;
(d) administration of a potentially therapeutic compound to the recipient mammal; and
(e) comparison of the effects of the compound on the development of T cell-mediated liver damage with a predetermined standard.

The recipient mammal may also be administered a T cell-activating agent after transfer of T cells from the donor, if this is required.

Preferably the mammal referred to herein is a rodent and most preferably the rodent is a rat. However, it will be appreciated by those of ordinary skill in the art that various other mammals may be used in the present invention.

Preferably the hepatic disorder is induced by migration of T lymphocytes to the liver. More preferably, the hepatic disorder is alcoholic hepatitis.

Preferably the T lymphocytes secrete TNFα.

Where referred to herein the agents known to induce hepatic disorder preferably include alcohol and a cofactor. Preferably, said cofactor is a T cell activating agent. In the case where alcohol is specifically administered first in the method the mentioned agent known to induce a hepatic disorder subsequently administered is a T cell activating agent.

Where alcohol is used in the methods of the present invention, the alcohol is preferably administered as a solution of ethanol in water. Preferably the solution contains 2 to 40% ethanol (v/v). Most preferably the solution contains 5 to 40% ethanol (v/v). Preferably the mammals are fed increasing concentrations of ethanol over a period sufficient to allow adaptation to the ethanol. Preferably the concentration of alcohol ranges from approximately 5% ethanol in water (v/v) to approximately 40% ethanol in water (v/v) over the period of adaptation. Preferably the period of adaptation is approximately seven weeks.

Where a cofactor is referred to herein it is preferably a T cell activator. Preferably the T cell activators referred to herein are concanavalin A (Con A). However, it will be clear to the skilled addressee that other compounds may also be useful eg. endotoxin.

Preferably Con A is administered in a single dose. Preferably the single dose is 1 to 40 mg/kg body weight. More preferably the single dose is 5–30 mg/kg and most preferably the single dose is 20 mg/kg. Preferably Con A is dissolved in phosphate-buffered saline. Preferably the Con A is administered by injection.

Preferably the therapeutic compound referred to herein is envisaged to treat alcohol-induced hepatitis or a pathogen-mediated hepatic disorder. Reference to pathogen-mediated hepatic disorder refers to hepatic disorders resulting from viral or bacterial infection and the like; for example, hepatitis B or hepatitis C. However, it will be clear to the skilled addressee that other types of hepatic disorder are also contemplated including autoimmune hepatitis.

According to a seventh aspect the invention provides a mammal when used to identify a compound useful in the prophylactic or therapeutic treatment of a hepatic disorder utilising any one of the methods described herein.

According to an eighth aspect the invention provides a therapeutic compound or a therapeutic composition for use in the treatment of hepatic disorders when identified by the method of the any of the preceding aspects.

Preferably the compound contains at least one active ingredient which is useful for the treatment of alcohol-induced hepatitis or a pathogen-mediated hepatic disorder, as described above. However, it will be clear to those skilled in the art that treatment of other types of hepatic disorder are also contemplated.

According to a tenth aspect of the present invention there is provided the use of CH-100 in the treatment of a hepatic disorder; preferably alcohol-induced hepatitis.

CH-100 may be administered by any one of the following routes: oral, systemic (e.g., transdermal, intranasal or by suppository), or parenteral (e.g., intramuscular, intravenous or subcutaneous) administration. However, the preferred manner of administration is oral using a convenient daily dosage regimen which can be adjusted according to the degree of affliction. Compositions, containing CH-100 and any pharmaceutically acceptable excipients and the like, can take the form of, for example, tablets, pills, capsules, semi-solids, powders, sustained release formulations, solutions, suspensions, elixers, aerosols, or any other appropriate compositions. CH-100 may also be presented in a form in combination with other agents which may be beneficial to the human condition.

Preferably, CH-100 is administered to a mammal in need thereof orally according to the regimen described herein in the Examples. More preferably, a mammal, preferably a human, may be treated using the following regimen:

Oral administration of five doses of CH-100 (containing approximately 340 mg of active herbs) per day, over a six month period.

However, it will be appreciated by those of general skill in the art to which the present invention relates that the dose of CH-100 administered to a mammal and, in addition, the administration regimen, may vary according to the facts presenting in each case. Such factors which may need to be taken into consideration include: individual preference or tolerance to CH-100, the severity of the disease in a particular individual, stage in progression of the disease, whether administration is merely prophylactic, and general health of an individual, for example. Further, administration regimes may be adjusted to provide an optimum therapeutic response. For example, several divided doses may be administered weekly or monthly or at other suitable time intervals or, the dose may be proportionally reduced or increased as indicated by the exigencies of the situation. Furthermore, it will be appreciated that one may assess the exigencies of the situation by conducting liver function and haematological tests well known in the art.

In the context of the present invention, the term "adaptation to ethanol" includes within its meaning induction of acceptance of a solution of alcohol of a concentration not normally acceptable to the animal eg. approximately 40% alcohol (v/v) in the case of a rat.

As used herein, a pharmaceutically acceptable excipient means an excipient that is useful in preparing a pharmaceutical composition that is generally safe, non-toxic and neither biologically nor otherwise undesirable, and includes an excipient that is acceptable for veterinary use as well as human pharmaceutical use. A pharmaceutically acceptable excipient as used in the specification and claims includes both one and more than one such excipient.

The term "predetermined standard" as used herein refers to a control mammal subjected to substantially equivalent conditions (for example, environmental, calorific intake and the like) as an experimental mammal but to which administration of the potentially therapeutic compound is withheld. Preferably, a number of control mammals are utilised, each of which is administered a combination of the agent or agents known to induce a hepatic disorder, or no such agent. In such cases a number of experimental mammals subject to appropriate corresponding conditions will be utilised, as is described in the Examples to follow. Utilising this strategy aims to minimise misleading experimental effects which may result. It will be appreciated by those of general skill in the art to which this invention relates that it is preferable that the experimental procedure to which both the control mammals and experimental mammals are subjected to be run concurrently in order to further minimise experimental artefacts. However, the use of data obtained from a control mammal studied prior to, or after, the initiation of a method of identifying a potentially therapeutic compound according to the invention is also contemplated.

Further, it will be appreciated that reference herein to "treatment" is to be considered in its broadest context. The term "treatment" does not necessarily imply that a subject is treated until total recovery. Accordingly, "treatment" includes amelioration of the symptoms or severity of a particular condition or preventing or otherwise reducing the risk of developing a particular condition and as such encompasses prophylactic measures also.

BRIEF DESCRIPTION OF THE FIGURES

These and other aspects of the present invention, which should be considered in all its novel aspects, will become apparent from the following description, which is given by way of example only, with reference to the accompanying figures, in which:

Plasma lipopolysaccharide (LPS) levels were measured (as an indication of gut damage) at 0, 4 and 8 weeks after ethanol consumption followed by Con A injection, and compared with those from rats fed 2% sucrose or isocaloric sucrose drink, also followed by Con A injection. Results represent the mean±SE of LPS (pg/mL) for 4 animals. *$p<0.05$ and ** indicates $p<0.01$ for rats fed alcohol compared with control. Time 0 represents values from animals not injected Con A;

FIG. 2. Illustrates Plasma Alanine Aminotransferase (ALT) Levels in Plasma Following the Injection of Con A ALT levels were measured in plasma at various times from rats fed alcohol and compared with those from rats fed 2% sucrose or isocaloric sucrose drink following Con A injection. Results represent the mean±SE of alanine aminotransferase activity (U/L) for 4 animals. $p<0.01$ and * indicates $p<0.001$ for rats fed alcohol compared with control. Time 0 represents values from animals injected PBS;

DESCRIPTION OF THE INVENTION

The following description outlines the experimental basis for the invention and specifically exemplifies preferred forms of thereof.

EXAMPLE 1

Animal Model of Chronic Alcohol Administration

Female Wistar rats were obtained from the Central Animal House, University of Newcastle, NSW., Australia. Animals were housed in individual hanging wire cages in a controlled temperature environment with a 12 hr light-dark cycle and were allowed free access to rat chow and drink throughout the study. Animals (3–6 rats per group) were fed 40% ethanol in water (v/v), isocaloric sucrose or 2% sucrose according to the regimen described previously[12]. Alcohol consuming rats were initially fed a 5% ethanol in water (v/v) solution, for the first week, and were then offered an increasing concentration of ethanol in water to 40% ethanol during a six to eight week period to allow adaptation to the ethanol. In order to provide the same coloric intake to each rat in the isocaloric group of controls, chow and drinking solution were regulated according to the caloric intake of each rat in the isocaloric group. Animals were allowed rat chow and 2% sucrose solution adlibitum in the second control group. The animal protocol described in this study was approved by the animal research ethics committee of the University of Newcastle and performed in accordance with the committee guidelines.

EXAMPLE 2

Administration of Chinese Herbal Medicine

Chinese herbal medicine, CH-100 (Cathay Herbal Laboratories Pty Ltd., Surry Hills, Australia), contains 19 different traditional herbs and was used to demonstrate the function of the model. The combination (4 tablets/kg body weight/day) was mixed in 20–30 g of rat chow and was fed daily for 8 weeks after rats achieved 40% ethanol solution while maintaining the rats on 40% ethanol for the 8 week period.

EXAMPLE 3

Con A Induced Hepatitis Model

Concanavalin A (Con A) (Pharmacia AB, Laboratory Separation Division, Uppsala, Sweden) was administered to each rat via the tail vein in a dose of 20 mg/kg body weight dissolved in 300 μL of phosphate buffered saline (PBS, Bioscience, Sydney, Australia)'. Con A was injected after 8 weeks on 40% alcohol. The rats continued to have access to alcohol following Con A injection. Animals were weighed and sacrificed 24 hours after Con A administration. One group used as a control at time 0 did not receive Con A. The liver was perfused and then removed for determination of wet weight, histological examination and CD4$^+$ T cell studies.

EXAMPLE 4

Isolation of Intrahepatic Mononuclear Cells by Liver Perfusion

Rats were anaesthetised by means of an intraperitoneal injection of ketamine (Parnell Laboratories Pty Ltd. Alexandria, NSW., Australia) and Rompun (Bayer Australia Ltd Pyrrible, NSW., Australia) (1:1 v/v, 0.08–0.12 mL/100 g body weight). Livers were preperfused in situ through the portal vein with sterile PBS containing 0.1% ethylenediaminetetraacetic acid, EDTA (Prolabo 12 Rue Pelee, Paris, France) at a pressure of 10 cm $H_2O$ giving a flow rate of 10 mL/min to remove intrahepatic blood. They were then perfused with 300 mL of PBS/EDTA solution at a pressure height of 40 cm $H_2O$ (flow rate of 30 mL/min). The perfusate (approx. 300 mL) collected from the inferior vena cava was centrifuged at 1500 rpm for 15 min. After the supernatant was discarded, the cells were resuspended in 3 mL of RPMI 1640 medium containing 5% FCS (Trace Scientific, Sydney, NSW., Australia). The cell suspension was then layered onto a Ficoll/Paque density gradient (Pharmacia, Uppsala, Sweden). Following centrifugation at 1500 rpm for 20 minutes, the cells were harvested from the interface, washed three times with PBS before being resuspended in RPMI/5% FCS medium[14].

EXAMPLE 5

Isolation of Liver-Associated CD4$^+$ T Cells

Liver-associated lymphocytes were labelled with mouse anti-rat CD4$^+$ (W3/25) (Serotec, Oxford, UK) at 4C for 45 minutes. The cells were then washed twice in cold PBS by centrifugation at 250×g for 10 minutes. After centrifugation, cells were labelled with an optimal concentration of F(ab')$_2$ rabbit anti-mouse isotype-specific immunoglobulins conjugated with FITC-conjugated F(ab')$_2$ (DAKO, Glostrup, Denmark). After incubation for 20 minutes, the cells were resuspended in 3 mL of RPMI 1640. Finally, liver-associated CD4$^+$ T cells were separated using FAScan Cell Sorter. Cell viability was >99% as determined by trypan blue exclusion.

EXAMPLE 6

Cytokine Production by Liver-Associated Lymphocytes

Liver-associated CD4$^+$ T cells were cultured with Con A (5 μg/mL) at 1×10$^6$ cells per mL of RPMI 1640 medium containing 5% FCS, L-glutamine (2 mM), and penicillin/Streptomycin (50 μg/mL) in a 96 well flat-bottomed plate in an atmosphere of 5% $CO_2$ in air. After 24 hrs, the supernatants were collected, centrifuged and stored at −70° C. until use for TNF assays.

EXAMPLE 7

Cytokine Assays

TNF-α was measured using commercial ELISA kits (Genzyme Diagnostics, Cambridge, Mass., USA). The limit of sensitivity was 15 pg/mL.

EXAMPLE 8

Assay for Plasma Transaminase Activities

Plasma from individual rats was obtained at various time intervals after Con A injection. Plasma transaminase activity was measured by the standard photometric method using a bichromatic analyzer (Department of Biochemistry, John Hunter Hospital, Newcastle, Australia).

EXAMPLE 9

Plasma LPS Assay

Plasma was collected at week 0 when rats entered the experiment, and 4 and 8 weeks after 40% ethanol consumption. LPS levels were analysed using the method of limulus amebocyte lysate (Cape Code Inc, Woods Hole, Mass., USA). The tests were performed exactly according to the instructions provided by the manufacturer.

EXAMPLE 10

Hepatic Pathology and Immunohistopathology

The livers were fixed in 10% formalin, embedded in paraffin, sectioned, and stained with haematoxylin and eosin for histological examination. Immunostaining for CD4$^+$ and CD8$^+$ T cells was carried out using mouse monoclonal antibodies to CD4$^+$ and CD8$^+$ on cryostat sections. The sections were incubated with horse-radish peroxidase rabbit anti-mouse immunoglobulin, and then developed using an Avidin-biotin kit (Zymed, South San Francisco, Calif., USA). All histology and immunostaining sections were reviewed by two of the authors who were unaware of the status of the animal being examined.

Statistical Analysis

Results are expressed as mean±SE. Statistical analysis was performed using the Student's t test. p values less than 0.05 were considered statistically significant.

EXAMPLE 11

Figure 1:
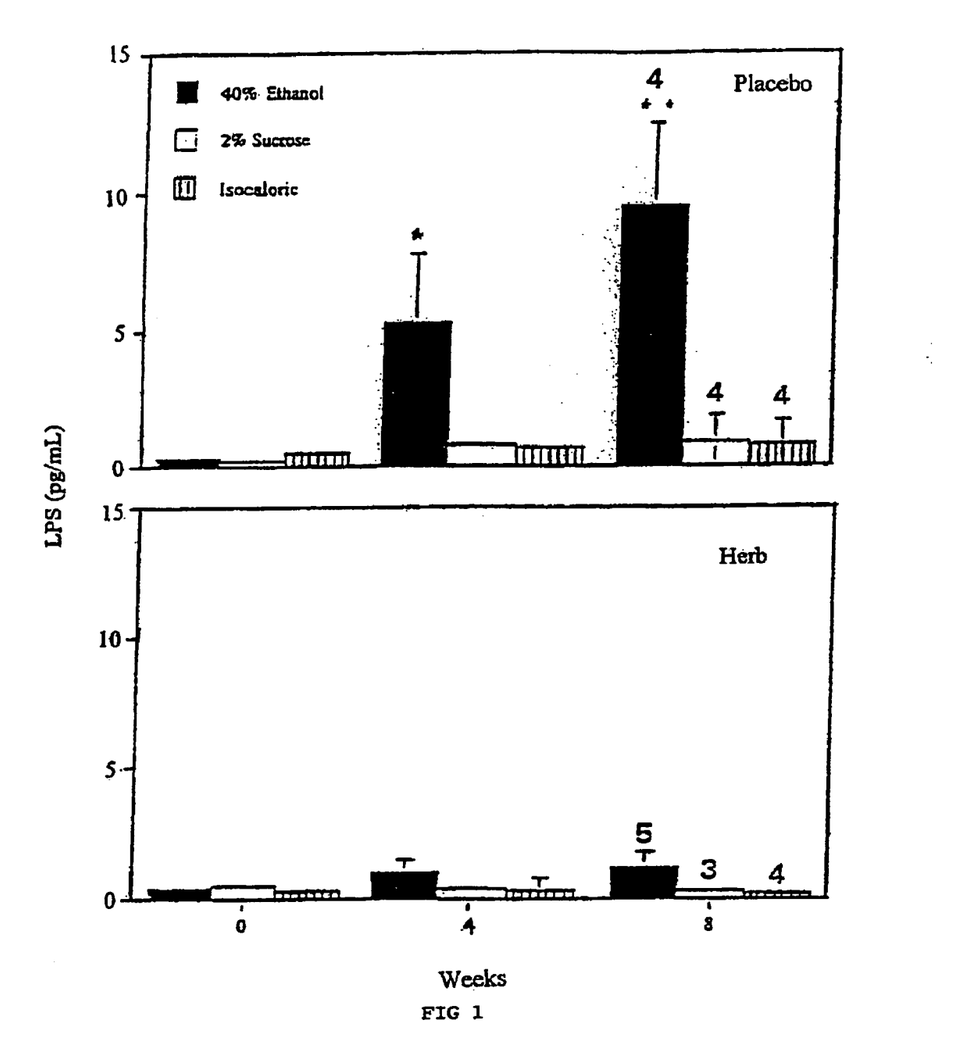
FIG. 1 Illustrates the Effects of Chinese Herbal Medicine on Plasma LPS Levels

Effect of Herbal Medicine on Body Weight Gain, Liver Weight, Ratio of Liver Weight to Body Weight and LPS Levels in Chronic Ethanol Consuming Rats Administered Con A Data of body weight, liver weight and ratio of liver weight to body weight were similar to our previous studies in ethanol-fed rats. Although liver weight and ratio of liver weight to body weight tend to decrease in ethanol-fed rats administered Con A after the treatment of herbal medicine, there was no significant difference (data not shown). Serum ethanol levels were consistently greater than 20 mmol/L in alcohol fed rats. Serum LPS levels were significantly elevated in ethanol-fed rats without herbal treatment compared with those in ethanol-fed rats with herbal treatment (FIG. 1).

EXAMPLE 12

Effect of Herbal Medicine on Plasma Transaminase Levels

Figure 2:
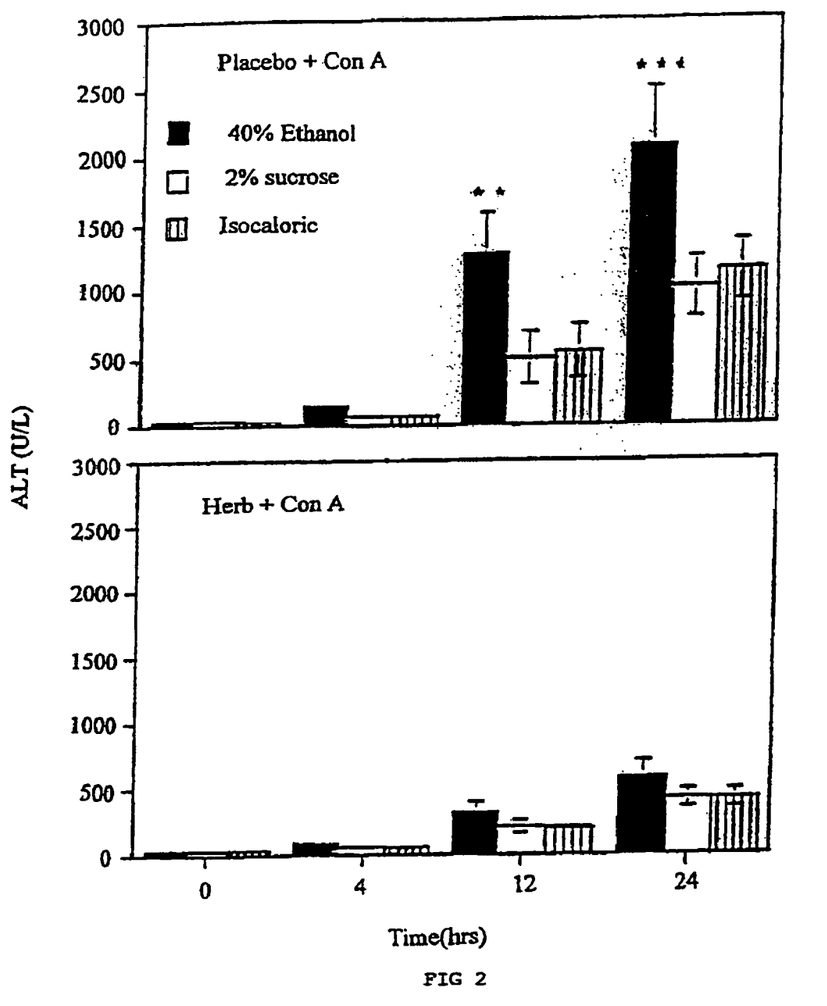

After injection of Con A, a significant increase in plasma transaminase levels (ALT) was detectable as early as 12 hr, with peak levels occurring at 24 hrs (FIG. 2) in placebo rats. The data show that plasma ALT levels in alcohol fed rats were higher than those in control animals ($p<0.01$), but there was no significant difference between 2% sucrose and isocaloric sucrose rats. In contrast, ALT levels were significantly lower in herbal treated rats (FIG. 2) ($p<0.01$).

EXAMPLE 13

Effect of Herbal Medicine on Serum TNPα Levels

Figure 3:
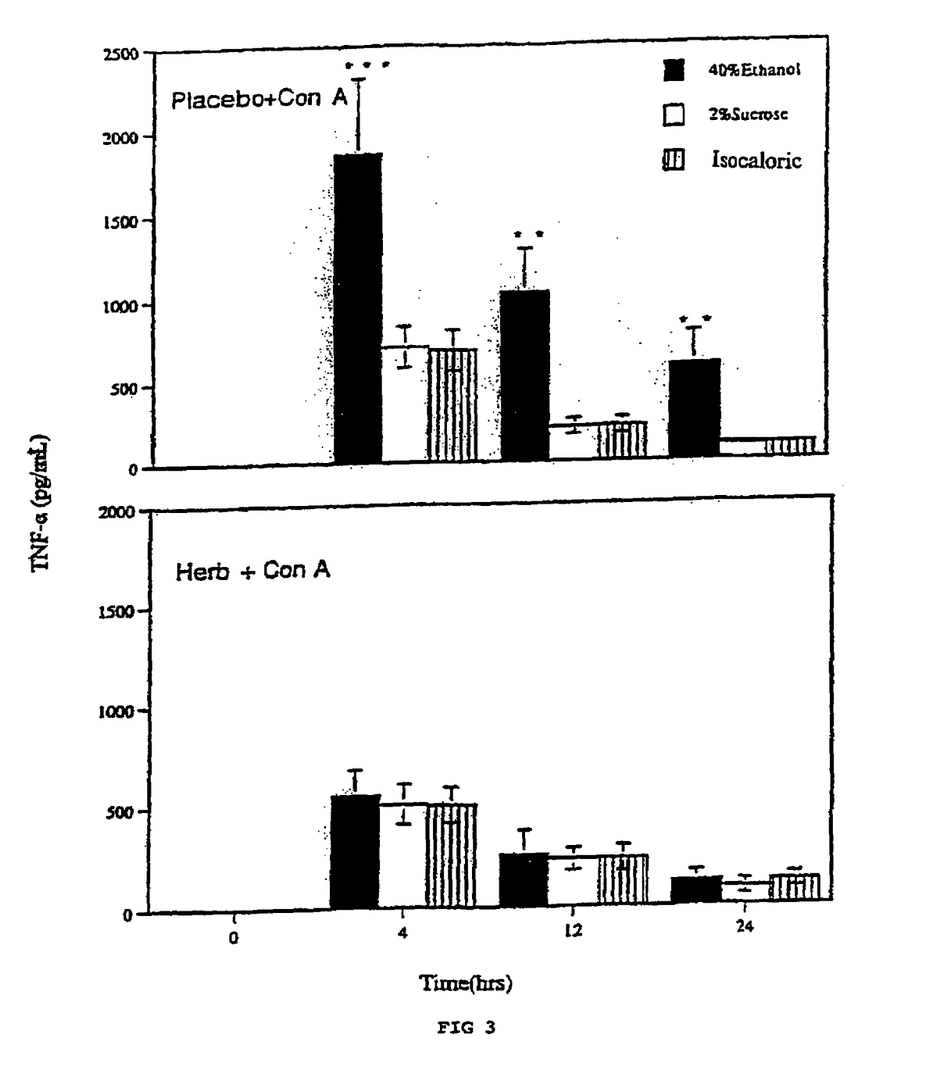
FIG. 3 Illustrates Serum TNF-$\alpha$ Levels in Herbal or Placebo-treated Rats Injected with Con A TNF-$\alpha$ levels were measured at various times in serum from rats fed alcohol and compared with those from rats fed 2% sucrose or isocaloric sucrose drink following Con A injection. Each point represents the mean±SE for 4 animals. $p<0.01$ and $p<0.001$ compared with control. Time 0 represents values from animals injected PBS.

A sharp increase in the serum levels of TNF-α was observed at 4 hr after Con A injection in all Con A treated animals without herbal treatment. This gradually declined to baseline levels after 24 hrs (FIG. 3). The data showed that following a single injection of Con A, a striking increase in the levels of serum TNF-α was detected earlier than the increase in plasma ALT levels. TNF-α in alcohol-fed rats were greater compared with the two sucrose control groups, but there was not significant difference between the two control groups (FIG. 3). Interestingly TNF-α levels were significantly lower in herbal treated rats than placebo-treated rats following Con A treatment (FIG. 3).

EXAMPLE 14

TNFα Secretion in Cultures of Liver-associated CD4+ T Cells

Figure 4:
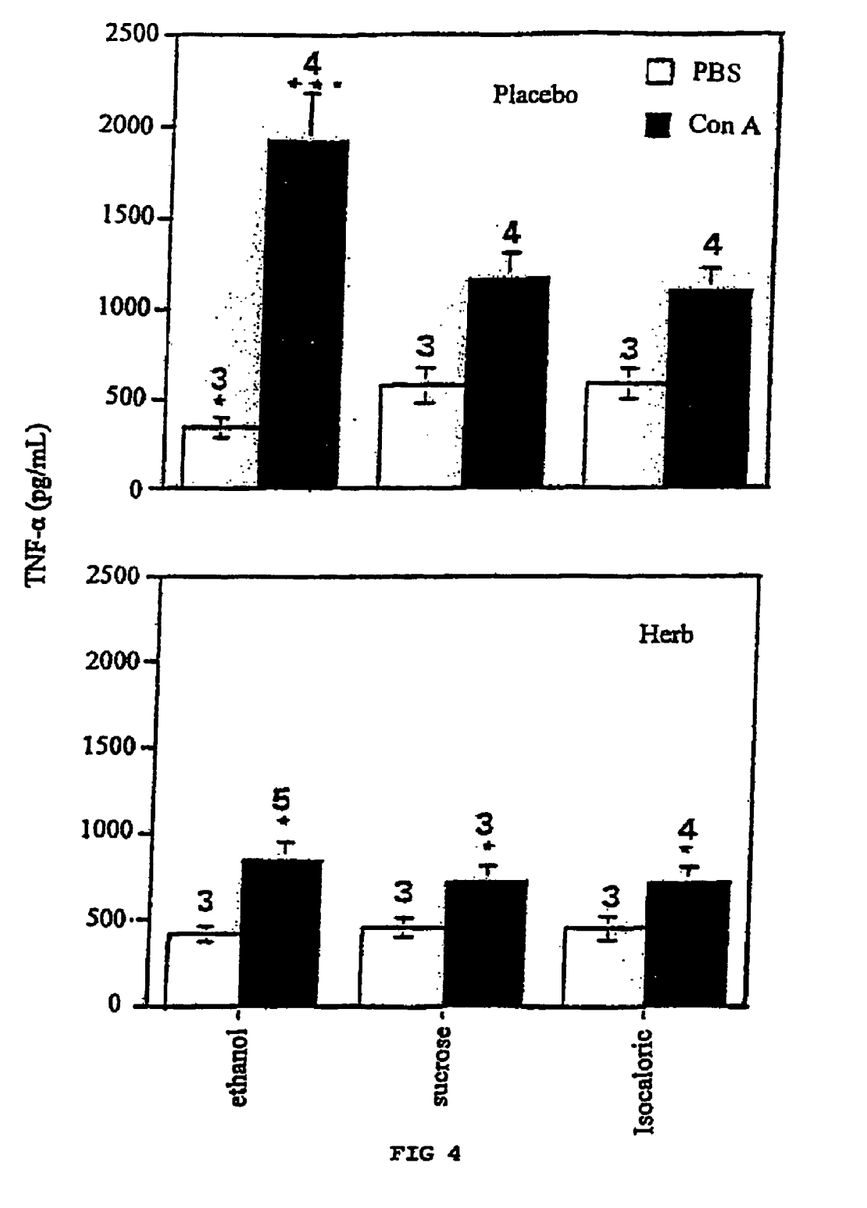
FIG. 4 Illustrates TNF-$\alpha$ Production by Liver-associated CD4$^+$ T Cells in Herbal or Placebo-treated Rats Following the Injection of Con A or PBS Liver-associated CD4$^+$ T cells isolated from rats at 24 hrs after injection of Con A or PBS were cultured in the presence of Con A (5 $\mu$g/mL). After 24 hrs, TNF-$\alpha$ were measured in culture supernatants. Each point represents the mean-SE for 4 animals. $p<0.05$ and $p<0.01$ compared with controls.

As shown in FIG. 4, the secretion of TNF-α by Con A stimulated liver-associated CD4+ T cells was significantly increased at 24 hr after Con A injection in placebo rats. TNF-α production by liver-associated CD4+ T cells was significantly increased at 24 hr after Con A injection in placebo rats. TNF-α production by liver-associated CD4+ T cells cultured with Con A were significantly higher in ethanol exposed rats receiving Con A without herbal treatment. In contrast, TNF-α levels secreted by CD4+ T lymphocytes were significantly lower in herbal treated rats than placebo rats following Con A injection.

EXAMPLE 15

Hepatic Pathology and Immunohistology

Under light microscopy, a score of 0–4 was recorded for the following: necrosis, cellular infiltration for zone 1, 2, 3 separately, and fatty change, and results are summarised in Table 1. In alcohol-fed rats without herbal treatment following Con A administration, changes in liver pathology were more marked with marked necrosis of hepatocytes accompanied by cellular infiltration compared with the two control groups. This consisted mainly of mononuclear cells and neutrophils in the portal areas, around the central vein and in hepatic lobules. Focal and lobular necrosis was seen with inflammatory cells found around the necrotic areas. The pathological changes were significantly decreased in herbal treated rats compared with placebo rats. Immunostaining with mouse anti CD4+ monoclonal antibodies revealed more CD4+ T cells in the portal area and the central vein areas 24 hrs after Con A injection in ethanol fed rats without herbal treatment than both groups of control rats. However, after herbal treatment, less CD4+ T cells were identified in ethanol-fed rats and both groups of control rats.

TABLE 1

Results of liver histology in animals fed CH 100 or placebo and treated as shown in the table.

| GROUP | | HERBAL MEDICINE | PLACEBO | |
| --- | --- | --- | --- | --- |
| Alcohol + ConA | n = 17 | 1.7 + 0.9 | 7.2 + 2.7 | p < 0.000 |
| Isocaloric + Con A | n = 4 | 31.9 + 0.6 | 5 | p < 0.44 |
| 2% + Con A | n = 6 | 3.8 + 1.5 | 8.3 + 2.0 | p < 0.001 |
| Alcohol + PBS | n = 3 | 0 | 0 | |
| Isocaloric + PBS | n = 3 | 0 | 0 | |
| 2% + PBS | n = 3 | 0 | 0 | |

EXAMPLE 16

Avoidance of Interference of Alcohol with Compound of Interest

The presence of alcohol in an animal may disturb the effects of certain compounds which would otherwise provide beneficial effects in the treatment of hepatic disorders. Since the model described above relies on T cell migration to the liver where damage is induced, it presents an opportunity to test such compounds. A donor rat is treated with alcohol and a T-cell activating agent as indicated above. Intrahepatic T cells are removed and injected into a recipient rat as described in Cao et al[15] the contents of which is hereby incorporated by reference. The recipient rat may be "primed" with the compound of interest prior to injection of the donor cells or may receive the cells and subsequently undergo treatment with the compound. Analyses are carried out in the manner described. Consequently, the need for alcohol administration to the recipient rats is alleviated and interference between the alcohol and compound of interest is avoided.

| COMPOSITION OF HERBAL MEDICINE, CH100 | |
|---|---|
| Herbal Components | mg (extract in 360 mg tablet) |
| *Artemisiafrigida* (plant) | 32 |
| *Saliva miltiorrrhiza* (root) | 32 |
| *Taraxacun mongolicum* (plant) | 28 |
| *Astragalua membranaccus* | 24 |
| *Loranthusparasiticus* (stem) | 24 |
| *Paeconia lactiflora* (root) | 24 |
| *Codonopsispilosula* (root) | 20 |
| *Glecchoma longituba* (plant) | 20 |
| *Polygonum cuspidatum* (root) | 20 |
| *Bupleurumfalcatum* (root) | 16 |
| *Crataeguspinnatifida* (fruit) | 16 |
| *Gentiana scabra* (whole fruit) | 16 |
| *Lycium babarum* (fruit) | 16 |
| *Zizyphusjujuba* (fruit) | 16 |
| *Curcuma longa* (fruit) | 16 |
| *Glycyrrhiza uralensis* (root) | 12 |
| *Polyporus umbelletus*(root) | 18 |
| *Poria cocos* (root) | 14 |
| *Pana-cpseudoginseng* (root) | 4 |

The invention has been described herein, with reference to specific examples, in order to enable the reader to practice the invention without undue experimentation. However, a person having ordinary skill in the art will readily recognise that many of the components and parameters may be varied or modified to a certain extent without departing from the scope of the invention and that the invention may be embodied in many other forms. Furthermore, titles, headings, or the like are provided to enhance the reader's comprehension of this document, and should not be read as limiting the scope of the present invention.

Finally, throughout this specification, and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

REFERENCES

1. Spinozzi F, Bertotto A, Rondoni F, Gerli I; -Scalise F, Grignani F: T lymphocyte activation pathways in alcoholic liver disease. Immunology 73: 140–146, 1991.
2. Roselle G A, Mendenhall C L, Chedid A, Moritz T E, Gartside P. The Veterans Affairs Cooperative Study Groups 119 and 275: Alcohol modulation of immune function: clinical and experimental data. Alcoholism: Clinical and Experimental Research 19(3): 551–554, 1995.
3. McKeever U, O'Mahony C, Whelan C A, Weir D O, Feighery C: Helper and suppressor T lymphocyte function in severe alcoholic liver disease. Clin Exp Immunol 60: 39–48, 1995.
4. Batey R, Cao Q, Madsen G, Pang G, Russell A, Clancy R. Decreased tumor necrosis factor-(x and interleukin-1 (x production from intrahepatic mononuclear cells in chronic ethanol consumption and upregulation by endotoxin. Alcoholism: Clin & Exp Res 22:150–156, 1998.
5. Cao Q, Batey R, Pang G, Clancy R. Altered T-lymphocyte responsiveness to polyclonal cell activators is responsible for liver cell necrosis in alcohol-fed rats. Alcoholism: Clin & Exp Res 22:723–729, 1998.
6. Cao Q, Batey R, Pang G, Russell A, Clancy R. IL-6, WN-y and TNF-α production by liver-associated T cells and acute liver injury in rats administered concanavalin A. Immunology and Cell Biology 76: 542–549, 1998.
7. Winnock M, Barcine M G, Lukomska B, Huet S, Saric J, Balabaud C, Biolac-Sage P: Human liver-associated lymphocytes: A review. J Gastroenterology and Hepatology 10: S43–S46, 1995.
8. Wang Y, Huang D S, Giger P T, Watson R R: Influence of chronic dietary ethanol on cytokine production by murine splenocytes and thymocytes. Alcoholism: Clin and Exp Res 18(1): 54–70, 1994.
9. Roselle G A, Mendenhall C L: tthan-ol-induced alterations in lymphocyte function in the guinea pig. Alcoholism: Clinical and Experimental Research 8(1): 62–67, 1984.
10. Chedid A, Mendenhall C L, Moritz T E, French S W, Chen T S, Morgan T R, Roselle G A, et al: Cell-mediated hepatic injury in alcoholic liver disease. Gastroenterology 105: 254–266, 1993.
11. Khorutus A, Stahnke L, McClain C J, Logan G, Allen fl: Circulating tumor necrosis factor, interleukin-1 and interleukin-6 concentrations in chronic alcoholic patients. Hepatology 13: 267–276, 1991.
12. Keegan A, Martini R, Batey R: Ethanol-related liver injury in the rat: a model of steatosis, inflammation and pericentral fibrosis. J Hepatology 23:591–600, 1995.
13. MizuEara H, O'Neil E, Seki N, Ogawa T, Kusunoki C, Otsuka K, Satoh S, et al: T cell activation-associated hepatic injury: mediation by tumor necrosis factors and protection by interleukin-6. J Exp Med 179:1529–1537, 1994.
14. Noble A, Macary P A, Kerneny D M: WN-y and IL-4 regulate the growth and differentiation of CD8-$^m$T cells into subpopulations with distinct cytokine profiles. J Immunology 155: 2928–2937, 1995.
15. Cao Q, Batey R, Pang G and Clancy R (1991) Etimol-modified T cell activation mediates liver injury in rats administered Con A. (in print)

What is claimed is:

1. A method of identifying a compound useful in the prophylactic or therapeutic treatment of a T cell mediated, pre-cirrhotic hepatic disorder in a mammal comprising:
    (a) administering to a mammal an agent or agents known to induce a T cell mediated, pre-cirrhotic hepatic disorder, wherein said agent or agents known to induce a T cell mediated, pre-cirrhotic hepatic disorder comprises alcohol and a T cell activating agent;
    (b) administering to said mammal a potentially therapeutic compound for down-regulating activated T cells;
    (c) comparing the effects of the compound on the development of the T cell mediated, pre-cirrhotic hepatic disorder in said mammal with a predetermined standard.

2. The method as claimed in claim 1, wherein said alcohol is administered as a solution of ethanol in water.

3. The method as claimed in claim 2, wherein said solution contains 2 to 40% ethanol (v/v).

4. The method as claimed in claim 3, wherein said solution contains 5 to 40% ethanol (v/v).

5. The method as claimed in claim 2, wherein said mammal is fed increasing concentrations of ethanol over a period sufficient to allow adaptation to the ethanol.

6. The method as claimed in claim 5, wherein said concentrations of alcohol range from approximately 5% ethanol in water (v/v) to approximately 40% ethanol in water (v/v), over a period sufficient to allow adaptation to the ethanol.

7. The method as claimed claim 6, wherein said period sufficient to allow adaptation to the ethanol is approximately seven weeks.

8. The method as claimed in claim 1, wherein said T cell activating agent is Concanavalin A.

9. The method as claimed in claim 8, wherein Concanavalin A is administered in a single dose of between 1 to 40 mg/kg body weight.

10. The method as claimed in claim 9, wherein the single dose is 5–30 mg/kg body weight.

11. The method as claimed in claim 10, wherein the single dose is 20 mg/kg body weight.

12. The method as claimed in claim 9, wherein said hepatic disorder is chronic hepatitis.

13. The method as claimed in claim 9, wherein said therapeutic compound inhibits liver cell necrosis by acting directly on T lymphocytes.

* * * * *

UNITED STATES PATENT AND TRADEMARK OFFICE
CERTIFICATE OF CORRECTION

PATENT NO. : 6,989,278 B1 Page 1 of 1
APPLICATION NO. : 09/959970
DATED : January 24, 2006
INVENTOR(S) : Robert Clancy, Robert Batey and Gerald Pang

It is certified that error appears in the above-identified patent and that said Letters Patent is hereby corrected as shown below:

Column 14, line 5 (Claim 12), change "claim 9" to -- claim 1 --.

Column 14, line 7 (Claim 13), change "claim 9" to -- claim 1 --.

Signed and Sealed this

Ninth Day of January, 2007

JON W. DUDAS
*Director of the United States Patent and Trademark Office*